United States Patent [19]

Sawai et al.

[11] Patent Number: 5,468,728
[45] Date of Patent: Nov. 21, 1995

[54] USE OF ORALLY ABSORBABLE MOTILIN PREPARATIONS TO ENHANCE MOTILITY OF DIGESTIVE TRACT

[75] Inventors: Kiichi Sawai; Masayasu Kurono; Takahiko Mitani; Makoto Sato; Hiroyuki Oowaki; Bunkichi Kato; Haruo Takahashi, all of Nagoya, Japan

[73] Assignee: Sanwa Kagaku Kenkyusho Co., Ltd., Nagoya, Japan

[21] Appl. No.: 117,653

[22] Filed: Sep. 8, 1993

Related U.S. Application Data

[63] Continuation of Ser. No. 860,471, Mar. 30, 1992, abandoned.

[30] Foreign Application Priority Data

Apr. 3, 1991 [JP] Japan .................. 3-071253

[51] Int. Cl.⁶ .................. A61K 38/00; C07K 5/00; C07K 7/00; C07K 17/00
[52] U.S. Cl. .................. 514/12; 514/13
[58] Field of Search .................. 514/12, 13

[56] References Cited

U.S. PATENT DOCUMENTS 4,917,893  4/1990  Okada et al. .................. 424/23
5,011,824  4/1991  Masada et al. .................. 514/13

FOREIGN PATENT DOCUMENTS

| 0369437 | 5/1990 | European Pat. Off. . |
| 0378078 | 7/1990 | European Pat. Off. . |
| 0437622 | 7/1991 | European Pat. Off. . |
| 9100739 | 1/1991 | WIPO . |
| WO92/01440 | 2/1992 | WIPO . |

OTHER PUBLICATIONS

Database WPIL, Section Ch, Week 9240, Derwent Publications Ltd., London, GB; Class B04, AN 92–328095 & JP–A–4 235 923 (Kyowa Hakko Kogyo KK), Aug. 25, 1992.

*Primary Examiner*—Jill Warden
*Assistant Examiner*—A. M. Davenport
*Attorney, Agent, or Firm*—Armstrong, Westerman, Hattori, McLeland & Naughton

[57] ABSTRACT

A readily absorbable type of motilin preparation containing a motilin-like active substance and a surface active agent is provided, in which the motilin-like active substance is mainly L-leucine-13-motilin-homoserine, and the surface active agent is selected from the group consisting of a bile salt, saponin and a polyethylene glycol higher-alcohol ether for nasal administration purposes and is a peptide lytic enzyme inhibitor for oral administration purposes.

2 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( i x ) FEATURE:
        ( A ) NAME/KEY: Region
        ( B ) LOCATION: 3
        ( D ) OTHER INFORMATION: /label=region
            / note="amino acid 3 denotes pro, gly, asn or ser"

( i x ) FEATURE:
        ( A ) NAME/KEY: Region
        ( B ) LOCATION: 8
        ( D ) OTHER INFORMATION: /label=region
            / note="amino acid 8 denotes gly, pro, asn or ser"

( i x ) FEATURE:
        ( A ) NAME/KEY: Region
        ( B ) LOCATION: 11
        ( D ) OTHER INFORMATION: /label=region
            / note="amino acid 11 denotes gln, glu or asp"

( i x ) FEATURE:
        ( A ) NAME/KEY: Region
        ( B ) LOCATION: 13
        ( D ) OTHER INFORMATION: /label=region -continued

```
         / note="amino acid 13 denotes an amino acid other
           than Met"

( i x ) FEATURE:
         ( A ) NAME/KEY: Region
         ( B ) LOCATION: 19
         ( D ) OTHER INFORMATION: /label=region
                 / note="amino acid 19 denotes asn, glu or asp"

( i x ) FEATURE:
         ( A ) NAME/KEY: Region
         ( B ) LOCATION: 22
         ( D ) OTHER INFORMATION: /label=region
                 / note="amino acid 22 denotes gln, lys or arg"

( i x ) FEATURE:
         ( A ) NAME/KEY: Region
         ( B ) LOCATION: 23..32
         ( D ) OTHER INFORMATION: /label=region
                 / note="Amino acid 23 denotes homoserine(inclusive
                   of homoserine-lactone) or amino acids 23-32 is and
                   polypeptide containing homoserine at the C-term.

( x i ) SEQUENCE DESCRIPTION: SEQ ID NO:1:

Phe  Val  Xaa  Ile  Phe  Thr  Tyr  Xaa  Glu  Leu  Xaa  Arg  Xaa  Gln  Glu  Lys
 1                    5                   10                           15

Glu  Arg  Xaa  Lys  Gly  Xaa  Xaa  Xaa  Xaa  Xaa  Xaa  Xaa  Xaa  Xaa  Xaa  Xaa
              20                   25                           30
```

USE OF ORALLY ABSORBABLE MOTILIN PREPARATIONS TO ENHANCE MOTILITY OF DIGESTIVE TRACT

This application is a continuation of application Ser. No. 07/860,471 filed Mar. 30, 1992, now abandoned.

BACKGROUND OF THE INVENTION

The present invention relates to a novel type of readily absorbable motilin preparation used to enhance the function of digestive tracts.

Motilin is a peptide hormone present in a digestive tract, which was for the first time isolated from the the mucous membrane of the upper region of the porcine small intestine and structurally determined by J. C. Brown et al. According to ordinary techniques, motilin is now generally extracted from the porcine gastroenteric tract, but its mass production is very difficult. Motilin production by chemical synthesis has also been practiced, but it is again difficult to obtain motilin in large amounts and at low costs on an industrial scale, because motilin contains 22 amino acids.

Applying biotechnology to motilin production is subject to a similar cost-effective problem, because sophisticated steps are needed for obtaining high-purity motilin. With a view to providing a solution to such problems, various motilin-related compounds have recently been synthesized for the stabilization and activity enhancement of motilin, including motilin analogues in which motilin is substituted at the 13-position by leucine or norleucine. We have also discovered and established one industrial way of producing them (see for instance EP-A-0378078A1 filed claiming the priorities of 06.01.89 JP 286/89; 24,08,89 JP216033/89; 24,08,89 JP 216034/89; and 08.11.89 JP 288730/89).

It is also well known that unstable motilins can be stabilized by pH regulation, stabilizers and other means, as set forth in EP-A-437622A1 filed claiming the priorities of 07.07.89 JP 176435/89 and 07.07.89 JP 176436/89. However, this publication provides nothing else than a disclosure of the possible application of known methods for stabilizing polypeptide substances to existing motilins and says nothing about how each substance is used or in what condition it is stabilized.

Motilin is known to have a physiological action on promoting the motility of digestive tracts and contracting the smooth muscles of digestive tracts. Prostaglandins are found to have an action on promoting the motility of digestive tracts as well, but they have a grave defect of having strong side effects. Hitherto, motilins have been expected to be used for promoting the motility of digestive tracts or for treating and diagnosing post-operation gastroenteropathies. Since the motilins are a sort of polypeptides, however, they have production and stability problems. In addition, they are found to be not absorbed in a living system when administrated thereto through administration (e.g., oral or suppository) routes other than injection, and offer a problem as to how their pharmacological action is produced. Thus, the motilins have been considered to be practically inefficacious in the form of pharmaceutics other than injections.

Until now motilins have been administrated to patients by injection, but this has some problems in that injection gives pain to the patients and those who can receive therapy are limited to in-patients.

We have already established an industrial way of producing motilin-like substances which are relatively stable and show strong action (our co-pending U.S. patent application specification) and, now taking this opportunity, we have made an additional investigation of ways for administrating motilins so as to solve the above problems. As a result, we have now found that the use of motilins in combination with specific surface active agents provides an administrating means that is at least equivalent to, or higher than, motilin injections in terms of effect. In other words, we have confirmed that after the oral or nasal administration of motilins combined with surfactants, there can be a remarkable effect on promoting the motility of digestive tracts; that is, the use of motilins combined with surfactants is efficacious for treating the dyskinesia of digestive tracts or contracting the smooth muscles of gastroenteric tracts after surgical operation.

As menitioned above, we have already established a genetic engineering way of producing proteins containing a motilin-like peptide sequence with high purity (see again our co-pending U.S. patent application Serial No. specification).

SUMMARY OF THE INVENTION

A main object of this invention is to provide a readily absorbable type of motilin preparation containing a motilin-like active substance and a surface active agent, which is administrated to patients through a route (e.g., an oral or nasal route ) other than inject ion.

PREFERRED EMBODIMENTS OF THE INVENTION

For the motilin-like polypeptide used in this invention, it is preferred to use a compound produced by the above-described method and having the general formula (1), given just below, in view of pharmacological activity and stability. However, note that the present invention is not limited to this compound, because even existing motilins, although slightly poor in absorptivity, may be used well enough.

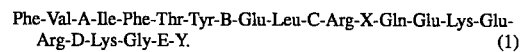

$$\text{Phe-Val-A-Ile-Phe-Thr-Tyr-B-Glu-Leu-C-Arg-X-Gln-Glu-Lys-Glu-Arg-D-Lys-Gly-E-Y.} \tag{1}$$

Here A denotes Pro, Gly, Asn or Ser,

B denotes Gly, Pro, Asn or Ser,

C denotes Gin, Glu or Asp,

D denotes Asn, Glu or Asp,

E denotes Gln, Lys or Arg,

X denotes an amino acid residue other than Met, and

Y denotes homoserine (inclusive of homoserine-lactone—hereinafter "Hse" for short) or any polypeptide containing homoserine at the C-terminal and having ten or less amino acids.

The surface active agents used with the readily absorbable motilin preparations of this invention enable the motilin-like substance to be well absorbed in the affected part by dispersing it moderately throughout the affected part and thereby expanding its tissue. For the pharmaceutical preparation to be administrated by way of a nasal route, various substances showing surface activity, such as those based on triterpenes, steroids and glycol higher-ethers, may be used as the surface active agent. For the purpose of inhibiting such side effects as the congestion of tunica mucosa of nose associated with long-term use as much as possible, however, it is preferable to use metal salts of bile acid (e.g., sodium deoxychlolate), saponins and polyoxy-ethylene glycol higher-alcohol ethers (e.g., polyoxyethylene lauryl ether).

For the pharmaceutical preparation to be administrated through an oral route, use may be made of peptide lyric enzyme inhibitors, e.g., a trypsin inhibitor such as papain, but synthetic compounds such as Gabexate, guanidinobenzoic acids and acidic polysaccharides such as dextran sulfate may be used as well. Usable surface active agents may be nonionic surfactants such as polyoxyethylene sorbitan fatty acid esters and sucrose fatty acid esters.

Although varying in dependence upon the type of the motilin-like substance administrated, the pharmaceutical preparations of this invention may be administrated to an adult at a dosage lying in the range of usually 1–100 mg for oral administration and in the range of usually 1–10 mg for nasal administration, when calculated as L-leucine-13-motilin-homoserine. The pharmaceutical preparations of this invention may be selectively formed into prompt and sustained action formulations in ordinary manners and using vehicles. In this case, use may additionally be made of pharmaceutically acceptable buffers, stabilizers, preservatives, dissolution aids, pH regulators, isotonicity agents and so on. For oral administration they may be used in the form of tablets, capsules, buccals or troches, and for nasal administration they may be used in the form of absorbable sprays, solutions and powders or suppositories.

The present invention will now be explained more specifically, but not exclusively, with reference to the following examples.

EXAMPLES

Preparative Example

Preparation of L-leucine-13-motilin-homoserine

Cells, which had produced a fused protein containing a motilin-like peptide, were suspended in cold acetone, and the suspension was then filtrated to obtain residues which were in turn air-dried into solid matter ( acetone powders ). Three hundred and fifty (350) g of this solid were suspended in 80 liters of physiological saline and crushed at a high pressure of 400 kg/cm$^2$ or more with a high-pressure homogenizer. The thus crushed cells were continuously centrifuged with a De Laval centrifuge to concentrate a fraction containing insoluble substances to less than 10 liters. Added to the resulting solution were white sugar and purified water to prepare a 0.5M white sugar solution, which was then continuously centrifuged to pelletize insoluble precipitates for recovery. The pellet is found to contain the motilin-like peptide containing fused protein.

The obtained precipitates were suspended in purified water to prepare an 8.6-liter suspension, to which 20 liters of formic acid were added to dissolve the precipitates. Subsequently, the solution was allowed to react with 75 g of cyanogen bromide at about 30 overnight. Following addition of 3 liters of purified water to the reaction solution, 40 liters of a 5N aqueous solution of sodium hydroxide were slowly added to the solution while it was cooled with cooling water. The thus neutralized solution was allowed to stand for about 1 hour and then subjected to centrifugation and filtration with a 0.3μm-pore size filter for removal of precipitates.

The thus purified neutralized solution was passed through a carrier column (φ9 cm×80 cm) for hydrophobic chromatography, which had been buffered with a 50% saturated ammonium sulfate, thereby adsorbing L-leucine-13-motilin-homoserine. After this, the column was washed with a 50% saturated ammonium sulfate and eluted with a 0.5% acetic acid to obtain an L-leucine-13-motilin-homoserine at a main peak detected at a 280-nm absorbance.

The eluate was desalted with an electrical dialyzer ("Microacilizer G3" made by Asahi Chemical Industry Co., Ltd.) until a current value of 0.1 A was obtained at a voltage of 7.5 V, said dialyzer using a styrene membrane having a fraction molecular weight of 300 and an effective membrane area of 400 cm$^2$ and a solution containing about 1% of ammonium sulfate as a dialysis liquid. The thus desalted solution was passed through a carrier S-Cephalose FF (φ14 cm×20 cm) for cation exchange chromatography, which had been buffered with a 0.5% acetic acid, then washed with a solution of a 0.25% acetic acid containing 50 mM acetic acid regulated to about pH 5 with NaOH, and finally eluted with a solution of a 0.25% acetic acid containing 350 mM salt regulated to about pH 5 with NaOH, thereby obtaining a fraction containing L-leucine-13-motilin-homoserine at a main peak detected at a 280-nm absorbance.

A 5N sodium hydroxide solution was slowly added to the eluate to regulate its pH to about 10, and the resulting solution was treated over a warm bath of about 37, immediately followed by addition of a phosphate buffer of pH 6 at a 20 mM concentration for neutralization. One hundred (100) ml of the thus treated solution were poured on an ODS column carried on silica (5 cm×25 cm, a pore size of 120 Å and a particle size of 10μm) which had been buffered with a 19% aqueous solution of acetonitrile containing a 0.012N hydrochloric acid and then eluted at a flow rate of about 60 ml/min.

Continuous measurement was done at 220 nm with an UV detector having an optical path length of 3 mm. The end L-leucine-13-motilin-homoserine started to elute. When the detector showed an absorbance of 0.1, a 22% aqueous solution of acetonitrile containing a 0.012N hydrochloric acid was obtained from this eluate, and fractionation was done at an absorbance of 0.5 or more to obtain a fraction containing L-leucine- 13-motilin-homoserine, immediately followed by addition of a phosphate buffer of pH 7.5 for neutralization. Similar procedures were repeated to separate all the portions by HPLC.

In this case, the column was washed with a 50% acetonitrile and then re-buffered. Five portions neutralized by HPLC were diluted with purified water about twice and then poured on a prepacked cartridge deltapack (made by Waters Co., Ltd.; and 4.7 cm×30 cm, a particle size of 15μm, a functional group C18 and a pore size of 100 Å) which had been buffered with a 0.003N hydrochloric acid. After washed with a similar solution, elution was done with a 80% aqueous solution of acetonitrile containing a 0.002N hydrochloric acid, thereby obtaining L-leucine-13-motilin-homoserine at a main peak. Immediately thereafter, this solution was neutralized with 10 mM of a phosphate buffer of pH 7.5. Similar procedures were repeated to subject all the HPLC fractions to column concentration.

In this case, the column was washed with a 50% acetonitrile and then re-buffered. This fraction was cleared of a large portion of the organic solvent by evaporator concentration and freeze-drying. The thus obtained peptide was dissolved in purified water at a peptide concentration of 2%, and then desalted by electrodialysis using a membrane having a fraction molecular weight of 300 and an effective membrane area of 400 cm$^2$ and using a solution containing about 1% of ammonium sulfate as a dialysis liquid until a current value of 0.01 A or less was obtained at a voltage of 7.5 V, whereby a solution containing high-purity L-leucine-13-motilin-homoserine. The yield of the thus obtained L-leucine-13-motilin-homoserine was 20 g or more when calculated as peptide with a purity of 99% or more. The quantity of endotoxin was determined to be less than the detection limit by limulus testing.

Examples of Pharmaceutical Preparations

I. Nasal Administration Type of Preparations

Example I-1 (Preparation dissoluble in use)

Added to 5 ml of a solution containing 3 mg of L-leucine13-motilin-homoserine were 30 mg of sodium gluconate and 100 mg of mannitol. The mixed solution was freeze-dried to obtain a nasal administration type of preparation which is dissoluble in use.

Example I-2 (Finely powdered preparation)

Added to 10 ml of a solution containing 30 mg of porcine motilin were 20 mg of polyoxyethylene cetyl ether and 100 mg of human serum albumin, followed by spray drying. The dried matter was sieved by a 100-mesh sieve to obtain a nasal administration type of powdery preparation.

Example I-3 (Finely powdered preparation)

Added to 15 ml of a solution containing 30 mg of L-leucine13-motilin were 25 mg of polyoxyethylene lauryl ether and 100 mg of human serum albumin, followed by spray drying. The dried matter was sieved by a 100-mesh sieve to obtain a nasal administration type of powdery preparation.

Example I-4 (Liquid preparation)

Fifty (50) mg of saponin were dissolved in 5 ml of a solution containing 5 mg of L-leucine-13-motilin homoserine to prepare a nasal administration type of liquid preparation, which is administrated to a patient by rhinenchysis or spraying.

Example I-5 (Hydrogel preparation)

According to the following recipe, a hydrogel preparation was prepared in ordinary manners and packed in an aluminium tube.

| | |
|---|---|
| L-leucine-13-motilin-homoserine | 300 mg |
| Hydroxypropylmethylcelluose | 0.1 g |
| Polysorbate 60 | 0.1 g |
| Gelatin | 0.5 g |
| 70% Sorbitol solution | 2.0 g |
| Citric acid | 0.1 g |
| Monobasic sodium phosphate | 0.3 g |
| Sodium chloride | 0.5 g |
| Benzalkonium chloride | 0.02 g |
| Purified water | suitable amount |
| Total: | 100 g |

Example I-6 (Nasal suppository)

The fine-powdery preparation of Example I-3 was added to and mixed with a glycerogelatin suppository base, whereby 50 mg of a nasal suppository containing 1 mg of the motilin-like substance was formed in ordinary manners.

II. Oral Administration Type of Preparations

Example II-1 (Granules)

A 1 g dosage of a granule preparation was prepared by mixing together 5 mg of L-leucine-13-motilin-homoserin, 10 mg of Gabexate and 200 mg of sucrose palmitate, adding to the mixture suitable amounts of lactose, starch and hydroxypropyl-cellulose, granulating the product and coating the granules with an enteric HPMCP in ordinary manners.

Example II-2 (Tablets)

The following ingredients were tableted together a vehicle in ordinary manners to obtain a tablet.

| Ingredients | |
|---|---|
| L-leucine-13-motilin-homoserine | 10 mg |
| Sodium lauryl sulfate | 20 mg |
| Carboxymethylcellulose (Ca) | 7 mg |
| Crystalline cellulose | 2 mg |
| Magnesium stearate | 7 mg |
| Lactose | suitable amount |
| Total: | 200 mg |

III. Pharmacological Activity Testing

Example III-1 (Animal Testing)

L-leucine-13-motilin (A) and L-leucine-13-motilin-homoserin (B) were administrated to dogs through an intravenous route ( 2.0 µg/kg/hr) and a nasal route (500 µg/kg/hr) by the ballon method to determine their activities on the contraction of the intestinal tracts, and the action of the surface active agent on promoting the absorption of the active substances administrated through a nasal administration was estimated in terms of percentage relative to the activity—100%— of L-leucine-13-motilin administrated through an intravenous route on the contraction. The results are set out in Table 1, which reveals that the addition of the surface active agent promotes well the absorption of the active substances administrated through a nasal route.

TABLE 1

| Administration Route | Substances Administrated | |
|---|---|---|
| (dosage) | A | B |
| Intravenous Administration (2.0 µg/kg/hr) | 100 ± 0 | 115 ± 5 |
| Nasal Administration (100 µg/kg/hr) | | |
| Control (Injection) | No activity found | ≦30 |
| Example | | |
| I-1 | — | 120 ± 5 |
| I-3 | 80 ± 5 | — |
| I-4 | — | 100 ± 5 |
| I-5 | — | 120 ± 5 |
| I-6 | — | 110 ± 5 |

In view of dosage, it is also noted that the nasal preparations are made at least 5% higher in absorption than the injection preparation by the addition of the surface active agent.

Control—Injection Preparation

L-leucine-13-motilin-homoserine and L-leucine-13-motilin were each dissolved in purified water to prepare an aqueous solution, which was then aseptically poured into a vial in such a way that it contained the active substance in an amount of 1 mg when calculated as polypeptide. Each vial was finally sealed together and freeze-dried. For use, this vial is dissolved in physiological saline for injection.

Example III-2 (Action on Promoting the Egestion of Indigestibles)

For test animals, four groups of six-month-old male beagles weighing 8±1 kg were used, each consisting of three. What influence the test substance L-leucine-13-motilin-homoserine has on the egestion of indigestibles from the stomachs was investigated by the acetaminophene method. As it is the duodenum, not the stomach, where the acetaminophene is first absorbed, the egestion of indigestibles from the stomach can be investigated by measuring the in-serum acetaminophene concentration. Two hundred (200) ml of liquid food containing 1.0 g of acetaminophene were fed for 1–2 minutes to each animal which was fasted from the day before testing. Before and 15, 30, 45 and 60 minutes after feeding, the in-serum acetaminophene concentration was measured. Administration of the test substance and control (vehicle) was done simultaneously with feeding. The results are set out in Table 2, from which it is found that in the groups receiving 0.5 mg/kg or more of the test substance, the egestion of indigestibles from the stomachs was considerably accelerated. Note that the test substance used was a pulverized form of the tablet according to Example II-2.

TABLE 2

| Test Groups | In-Serum Acetaminophene Concentration (µg/ml) | | | |
|---|---|---|---|---|
| | 15 min. | 30 min. | 45 min. | 60 min. |
| Control (Lactose) | 2 | 8 | 12 | 17 |
| 1.01 mg/kg Group | 2 | 9 | 11 | 17 |
| 0.5 mg/kg Group | 3 | 11 | 21 | 24 |
| 5.0 mg/kg Group | 2 | 12 | 23 | 26 |

The readily absorbable preparations containing motilin-like substances according to this invention are somewhat inferior to injections in terms of dosage, but by making use of the well-established mass production of motilin-like substances, there can be provided pharmaceutical preparations and methods of administrating them, which are expected to be equivalent in effect to injections. The pharmaceutical preparations of this invention are not only unlikely to give pain to patients, but can be used by patients themselves as well. Thus, they can be widely used as drugs for digestive tracts.

---

What is claimed is:

1. A method of enhancing motility of the digestive tract in a mammal which comprises orally or nasally administering to a mammal in need of such enhancement a pharmaceutical preparation comprising a peptide exhibiting motilin activity, a peptide lyric enzyme inhibitor and a surface active agent.

2. A method according to claim 1, wherein the peptide exhibiting motilin activity is L-leucine-13-motilin-homoserine or a peptide of the formula Phe-Val-A-Ile-Phe-Thr-Tyr-B-Glu-Leu-C-Arg-X-Gln-Glu-Lys-Glu-Arg-D-Lys-Gly-E-Y wherein A denotes Pro, Gly, Asn or Ser, B denotes Gly, Pro, Asn or Ser, C denotes Gln, Glu or Asp, D denotes Asn, Glu or Asp, E denotes Gln, Lys or Arg, X denotes an amino acid residue other than Met, and Y denotes homoserine, homoserine-lactone or a polypeptide containing homorserine at the C-terminal and having ten or less amino acids.

* * * * *